United States Patent
Griesel et al.

(10) Patent No.: US 10,039,679 B2
(45) Date of Patent: Aug. 7, 2018

(54) OPERATING UNIT FOR A MEDICAL APPARATUS

(71) Applicant: Trumpf Medizin Systeme GmbH + Co. KG, Saalfeld (DE)

(72) Inventors: Andre Griesel, Saalfeld (DE); Falk Georgi, Saalfelder Hoehe (DE); Christopher Schmotz, Uhlstaedt-Kirchhasel (DE); Thomas Deutscher, Koenigsbrueck (DE); Joerg Meissner, Jena (DE)

(73) Assignee: TRUMPF MEDIZIN SYSTEME GMBH + CO. KG, Saalfeld (DE)

( * ) Notice: Subject to any disclaimer, the term of this patent is extended or adjusted under 35 U.S.C. 154(b) by 496 days.

(21) Appl. No.: 14/710,923

(22) Filed: May 13, 2015

(65) Prior Publication Data

US 2015/0245965 A1 Sep. 3, 2015

Related U.S. Application Data

(63) Continuation of application No. PCT/EP2013/073650, filed on Nov. 12, 2013.

(30) Foreign Application Priority Data

Nov. 13, 2012 (DE) .................. 10 2012 220 667

(51) Int. Cl.
*A61G 7/018* (2006.01)
*A61G 7/015* (2006.01)
(Continued)

(52) U.S. Cl.
CPC ............ *A61G 7/018* (2013.01); *A61B 6/0407* (2013.01); *A61B 6/0457* (2013.01);
(Continued)

(58) Field of Classification Search
CPC ........ A61G 7/005; A61G 7/012; A61G 7/015; A61G 7/018; A61G 13/04; A61G 13/06;
(Continued)

(56) References Cited

U.S. PATENT DOCUMENTS

| 4,926,456 A | * | 5/1990 | Bock | ................ A61B 6/00 378/177 |
| 5,008,921 A | * | 4/1991 | Kaul | ................ A61B 6/4405 378/193 |

(Continued)

FOREIGN PATENT DOCUMENTS

| DE | 4224246 C1 | 8/1993 |
| DE | 19922258 A1 | 11/2000 |

(Continued)

OTHER PUBLICATIONS

Notification of Transmittal of Translation of the International Preliminary Report on Patentability and Written Opinion for corresponding PCT Application No. PCT/EP2013/073650, dated May 28, 2015, 8 pages.

(Continued)

*Primary Examiner* — Robert G Santos
(74) *Attorney, Agent, or Firm* — Barnes & Thornburg LLP

(57) ABSTRACT

This disclosure provides operating units for a medical apparatus having a driven movable element comprising a fixing device for being fixed to the movable element, an actuating element, a signal processing device, at least one actuation sensor for detecting an actuation of the actuating element in at least one predetermined actuation axis ($B_1^- - B_1^+$, $B_2^- - B_2^+$), wherein the actuation sensor is adapted to supply an actuation signal depending on a direction of actuation ($B_1^-$, $B_1^+$, $B_2^-$, $B_2^+$) in the actuation axis ($B_1^- - B_1^+$, $B_2^- - B_2^+$) to the signal processing device and at least one direction sensor for outputting a direction signal. The signal processing (Continued)

device is adapted to align an actuation coordinate system according to the direction signal such that the direction of movement is equal to the direction of actuation ($B_1^- - B_1^+$, $B_2^- - B_2^+$), and to supply a control signal according to the actuation signal in the aligned actuation coordinate system to a control device of the medical apparatus.

19 Claims, 6 Drawing Sheets

(51) Int. Cl.
| | |
|---|---|
| A61G 13/08 | (2006.01) |
| A61B 6/04 | (2006.01) |
| A61B 17/225 | (2006.01) |
| A61G 7/005 | (2006.01) |
| A61G 13/04 | (2006.01) |
| A61G 13/10 | (2006.01) |
| A61B 17/00 | (2006.01) |
| A61G 13/12 | (2006.01) |

(52) U.S. Cl.
CPC ......... *A61B 17/2255* (2013.01); *A61G 7/005* (2013.01); *A61G 13/04* (2013.01); *A61G 13/101* (2013.01); *A61B 2017/00199* (2013.01); *A61B 2017/00221* (2013.01); *A61G 7/015* (2013.01); *A61G 13/08* (2013.01); *A61G 13/1295* (2013.01)

(58) Field of Classification Search
CPC ...... A61G 13/08; A61B 5/0555; A61B 6/032; A61B 6/035; A61B 6/04; A61B 6/0407; A61B 6/0457
USPC ...... 5/610, 616, 601, 600; 378/193–196, 20, 378/177, 204, 208, 209
See application file for complete search history.

(56) References Cited

U.S. PATENT DOCUMENTS

| | | | | |
|---|---|---|---|---|
| 5,561,699 A | * | 10/1996 | Fenner | A61B 6/0457 378/204 |
| 6,045,262 A | | 4/2000 | Igeta et al. | |
| 6,422,241 B1 | | 7/2002 | Soukal | |
| 7,079,022 B2 | * | 7/2006 | Kagermeier | G05B 9/02 340/509 |
| 7,256,705 B2 | * | 8/2007 | Kagermeier | A61B 6/04 340/12.55 |
| 7,341,375 B2 | * | 3/2008 | Zaiki | A61B 6/0457 378/196 |
| 7,471,985 B2 | * | 12/2008 | Kagermeier | A61B 5/0002 128/903 |
| 7,664,557 B2 | * | 2/2010 | Danzer | A61B 6/0457 607/60 |
| 8,683,628 B2 | * | 4/2014 | Baumann | A61B 6/0457 297/135 |
| 2004/0125920 A1 | * | 7/2004 | Zaiki | A61B 6/0457 378/195 |
| 2004/0201287 A1 | * | 10/2004 | Kagermeier | G05B 9/02 307/326 |
| 2005/0004630 A1 | * | 1/2005 | Kagermeier | A61B 5/0002 607/60 |
| 2005/0017871 A1 | | 1/2005 | Kagermeier et al. | |
| 2007/0152508 A1 | | 7/2007 | Mezhinsky | |
| 2007/0200396 A1 | * | 8/2007 | Baumann | A61B 6/0457 297/135 |
| 2007/0200936 A1 | | 8/2007 | Terada | |
| 2008/0058967 A1 | | 3/2008 | Danzer et al. | |
| 2008/0172790 A1 | | 7/2008 | Brustmann | |
| 2009/0126115 A1 | | 5/2009 | Doering et al. | |
| 2009/0231179 A1 | | 9/2009 | Bruhn | |
| 2010/0068597 A1 | | 3/2010 | Hafemeister et al. | |
| 2011/0011708 A1 | | 1/2011 | Ellafrits | |
| 2015/0245965 A1 | * | 9/2015 | Griesel | A61G 7/005 5/607 |

FOREIGN PATENT DOCUMENTS

| | | |
|---|---|---|
| DE | 10311326 A1 | 9/2004 |
| DE | 102006008505 A1 | 8/2007 |
| DE | 102006040941 A1 | 3/2008 |
| DE | 102006060810 A1 | 6/2008 |
| DE | 102007014785 A1 | 10/2008 |
| DE | 102007060810 A1 | 6/2009 |
| EP | 1929986 A2 | 6/2008 |

OTHER PUBLICATIONS

German Office Action in related DE102012220667.1 application, dated Oct. 4, 2017, 5 pages.

\* cited by examiner

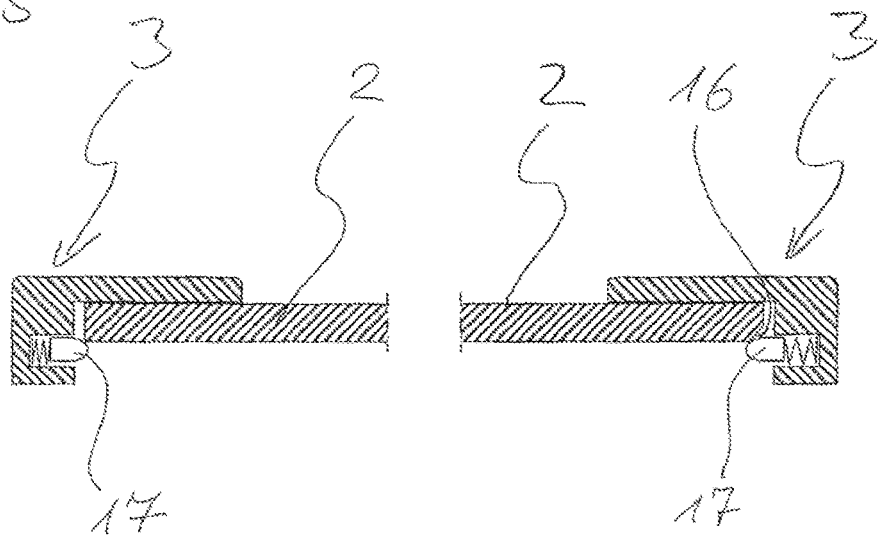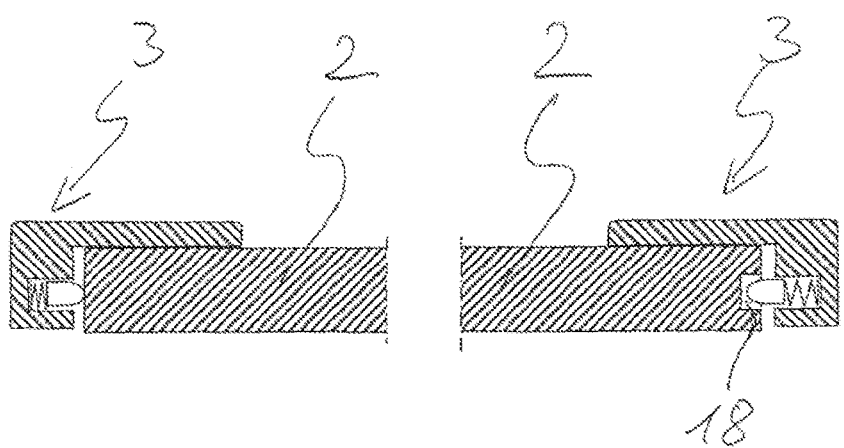

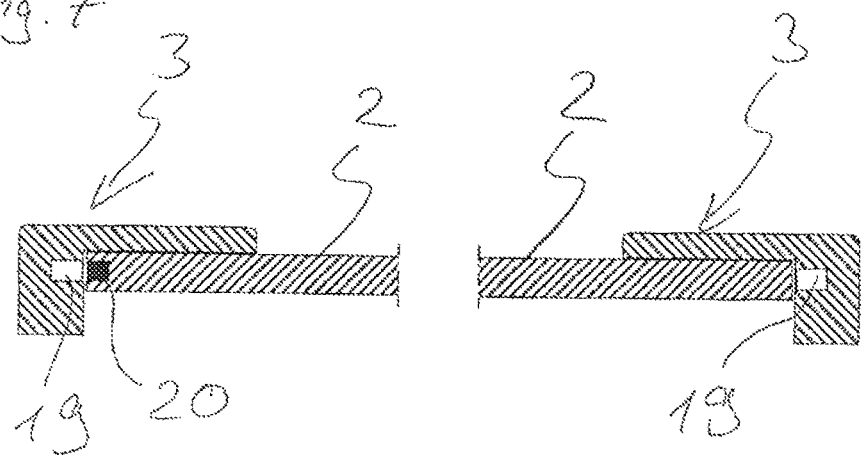
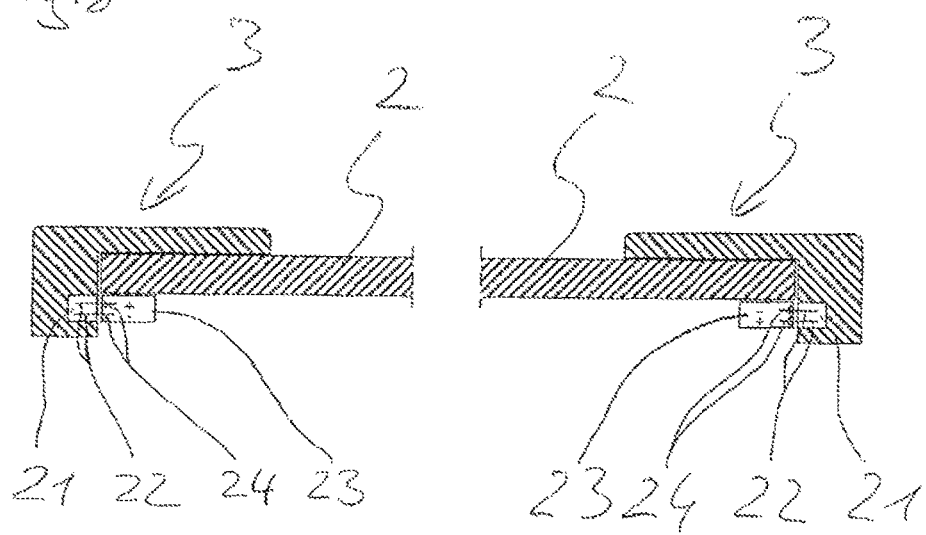

OPERATING UNIT FOR A MEDICAL APPARATUS

CROSS-REFERENCE TO RELATED APPLICATIONS

This application is a continuation of and claims priority under 35 U.S.C. § 120 to PCT Application No. PCT/EP2013/073650 filed on Nov. 12, 2013, which claimed priority to German Application No. DE 10 2012 220 667.1, filed on Nov. 13, 2012. The contents of both of these priority applications are hereby incorporated by reference in their entirety.

TECHNICAL FIELD

The present disclosure relates to an operating unit for a medical apparatus, and in particular, the present disclosure relates to an operating unit configured for attachment to different sides of a driven movable element of a medical apparatus.

BACKGROUND

Operating units may be attached to a driven movable element of a medical apparatus to control the movements of the driven movable element of the medical apparatus. For example, an operating unit configured to control the movements of a movable tabletop of a patient support table may be attached to the moveable tabletop. Once the operating unit is attached to the moveable tabletop, the operating unit may be activated, for example by exerting a force on the operating unit, to induce movement of the moveable tabletop. A handle of the operating unit may be pushed in a certain direction to permit displacement of the moveable element.

A particular patient or a particular treatment may benefit from examination on a particular side of the patient. The attachment of the operating unit on the side of examination or treatment may disadvantageously interfere with or impede access to the patient and examination or treatment of the patient on the side at which the operating unit is located.

SUMMARY

The configurability of an operating unit in a manner that permits the operating unit to be attached to a moveable element of medical device at different positions and at different sides of the moveable elements advantageously enhances the flexibility of the operating unit and the medical device. To change the displacement direction of the moveable element, for example to generate a longitudinal or a transverse displacement of a moveable element, such as a table top, the direction of actuation may be determined and the output of the operating unit may be adjust accordingly.

However, attaching the operating unit at different sides of the movable element introduces additional technical complexities associated with the orientation of the operating unit. In particular, because the direction of movement of the movable element may correspond to a direction of actuation of an actuating element of the operating unit when the operating unit is attached at to a first side of the moveable element, attachment of the operating unit to another side of the movable element opposite the first side reverses the operation of the operating unit with respect to a direction of movement of the moveable element.

Accordingly, various embodiments disclosed herein provide operating units having an actuating element configured to control a movable element of a medical apparatus such that a direction of actuation of the actuating element of the operating unit corresponds to a direction of movement of the movable element independent of a position at which the operating unit is attached to the moveable element of the medical apparatus.

According to an aspect of the disclosure, the operating unit for a medical apparatus configured for attachment to a driven movable element of the medical apparatus includes an actuation sensor and either a direction sensor or a contact device supplying a direction signal to a signal processing device. The signal processing device is adapted to compare the direction signal and the actuation signal, to align an actuation coordinate system according to the result of the comparison, and to supply a control signal according to the actuation signal in the aligned actuation coordinate system to a control device of the medical apparatus.

Various embodiments of the invention are further elucidated herein by descriptions of embodiments illustrated, at least in part, in the attached drawings.

DESCRIPTION OF DRAWINGS

FIG. 5 is a principle illustration of a detection of a first feature.

FIG. 6 is a principle illustration of a detection of a second feature.

FIG. 7 is a principle illustration of a detection of a third feature.

FIG. 8 is a principle illustration of a plug connection for a recognition of the sides.

DETAILED DESCRIPTION

Figure 1:
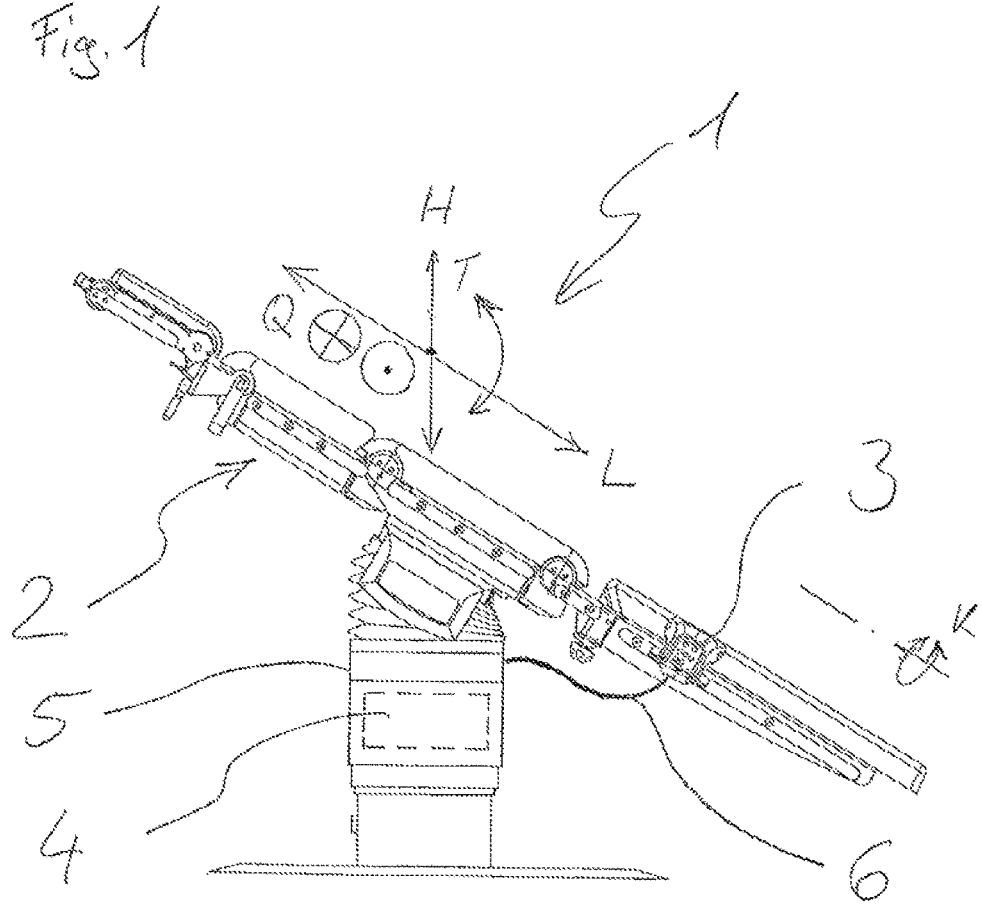
FIG. 1 is a side view of a surgical table in an Anti-Trendelenburg position with an operating unit attached thereto.

FIG. 1 shows a side view of a surgical table 1 as an example of a medical apparatus. Other medical apparatuses to which embodiments of the present disclosure can be applied to include, but are not limited to, driven adjustable patient support tables or other medical apparatuses on which several movements of a movable element can be adjusted in a driven manner. The surgical table 1 is shown in an Anti-Trendelenburg position. As described further herein, the surgical table 1 includes a moveable element movably coupling a surgical tabletop 2 to an operating unit 3.

The surgical table 1 further comprises a control device 4. The control device 4 controls movements of the surgical table 1, which movements are executed by drives (not shown). The drives are provided, at least in part, to adjust:

a height adjustment H, by which, the surgical tabletop 2 is adjusted in its height, a longitudinal displacement L, by, which the surgical tabletop 2 is displaced in a translational manner along its longitudinal axis, a tilt T into a Trendelenburg or Anti-Trendelenburg position by rotating the surgical tabletop 2 around its transverse axis (e.g. pitch), a transverse displacement Q, by which, the surgical tabletop 2 is displaced in a translational manner along its transverse axis, and a tilt K, wherein the surgical tabletop 2 is rotated around its longitudinal axis (e.g. roll).

The movements adjusted by the drives are initiated by an operating panel (not shown) at a column 5 of the surgical table 1. The movements may be controlled by a remote control (not shown), or by the operating unit 3, which causes activation of the drives. In various embodiments, the operating panel and/or the remote control may be optional. In various embodiments, the drives may include motorized drives coupled to a gear system. In various embodiments, the drives may include hydraulic or pneumatic drive components.

The operating unit 3 comprises a cable connection 6, communicably coupling the operating unit 3 to the control device 4. In various embodiments, the operating unit 3 is communicably coupled to the control device 4 via a wireless communication system. The wireless communication system may include, but is not limited to, an infrared or/and a radio connection.

Figure 2:
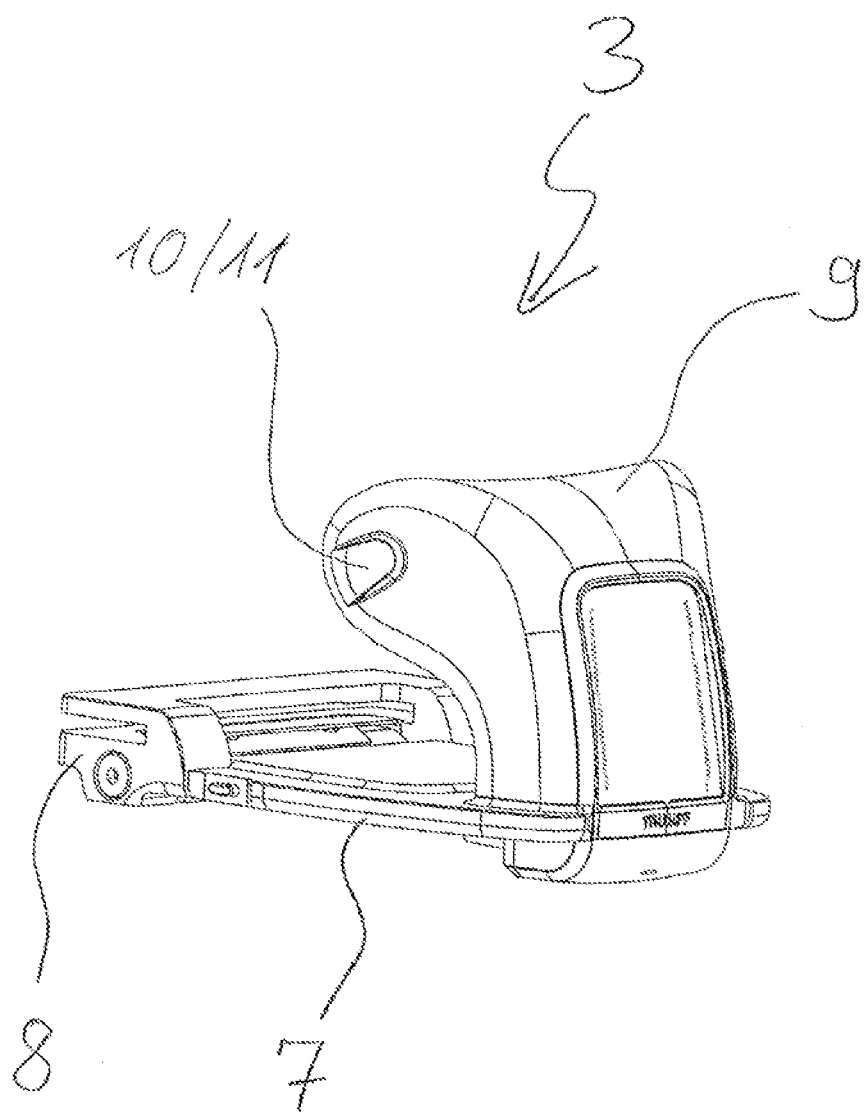
FIG. 2 is an isometric view of the operating unit.

The operating unit 3, shown in FIG. 2, comprises a base plate 7 connecting a fixing device 8 and an operating handle 9 to the surgical tabletop 2. The operating handle 9 serves as an actuating element. Other actuating elements (as, e.g., a sensor area) by which a direction of an actuation and, as the case may be, a magnitude of an actuating force may be specified are possible.

Figure 3:
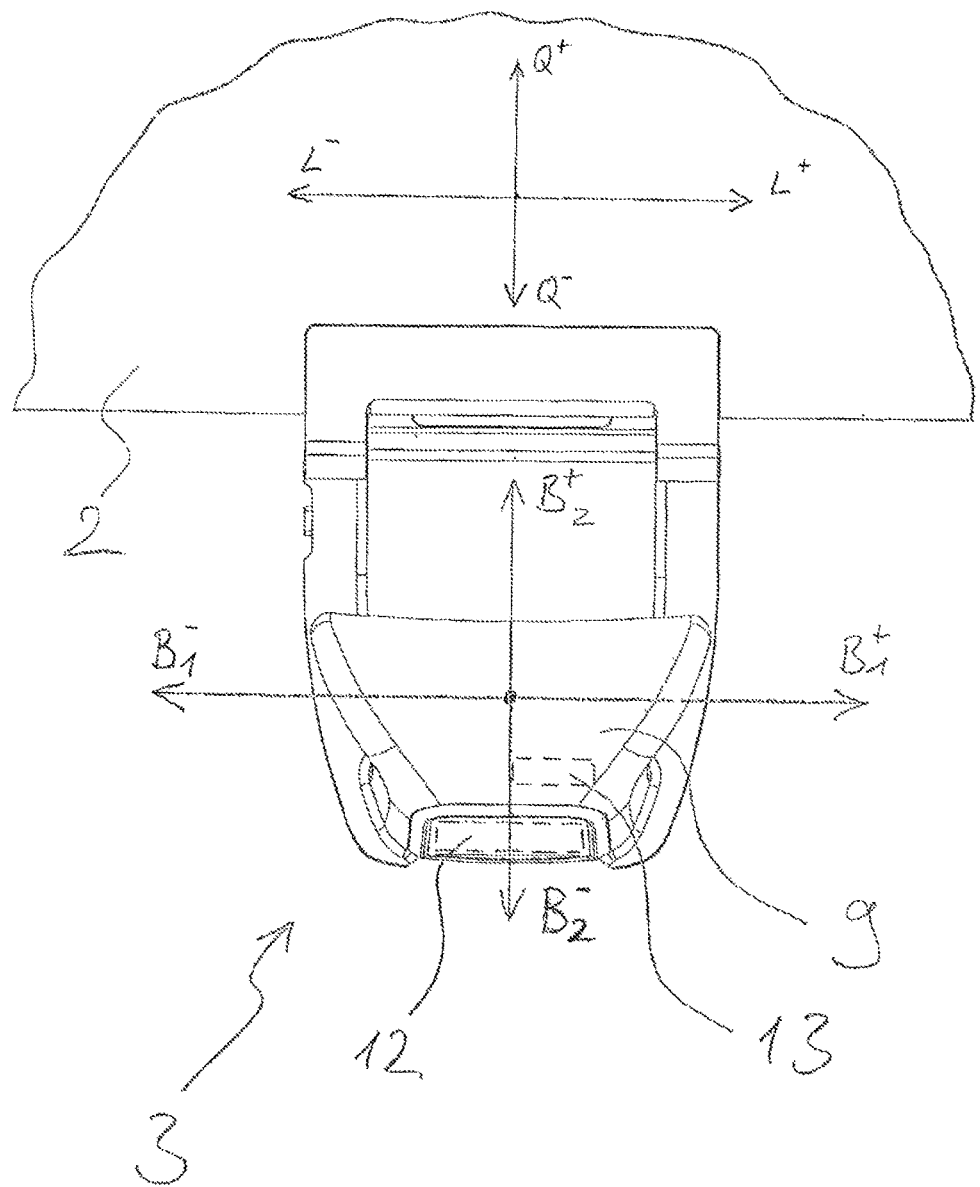
FIG. 3 is a plan view onto the operating unit.

The fixing device 8 couples the operating unit 3 to the surgical tabletop 2 (FIG. 1). The fixing device 8 is either, as shown in FIG. 3 and described below, clamped to a carbon plate as the surgical tabletop 2 (FIG. 1) by means of a clamping lever (not shown) or it is clamped to an adapter (not shown), which in turn is fixed to standard rails at the surgical tabletop 2. The clamping lever is secured against inadvertent releasing by means of a displaceable lock. In various embodiments, other clamping and anti-release devices may be provided as an alternative to or in addition to the clamping lever and displaceable lock. The clamping generally takes place without a tool to permit quick removal and attachment of the operating unit 3 from one location of the surgical tabletop 2 to another location of the surgical tabletop 2. While various embodiments are generally configured for clamping without a tool, certain embodiments may be clamped by means of a tool, for example a tool configured for attaching screws or fasteners.

The actuating element 9, includes a button 10 for activating a changeover switch 11 supplying a changeover signal to a signal processing device described further herein. The changeover signal provided by the changeover switch provides a basis for implementing a rotation of the surgical tabletop 2 (e.g., a tilt T and K or pitch and a roll) in response to a particular direction of actuation of the actuating element 9. Accordingly, the changeover signal is equivalent to a rotation signal and the signal causes rotation about the axis specified by actuation of the actuating element and in the direction specified by the actuating element and determined coordinate system alignment as described further herein. The button 10 is provided at such a location that when a hand of an operator encloses the actuating element 9 the thumb of the operator can actuate the button 10 in an ergonomic manner. Alternatively, another location for the changeover switch 11 and the button 10 may be implemented to permit actuation of the button 10 in an ergonomic manner and/or preclude or reduce unintentional presses.

FIG. 3 shows a plan view of the operating unit 3 and of a portion of the surgical tabletop 2. The operating unit 3 is clamped to the carbon plate as the surgical tabletop 2 here.

The surgical tabletop 2 can be adjusted respectively in a direction L- and L+ by the longitudinal displacement L. The surgical tabletop 2 can be adjusted by the transverse displacement Q in a direction Q- and Q+. Since the operating unit 3 is fixed to the surgical tabletop 2, the control device 4 can cause adjustments of the surgical tabletop 2 longitudinally and transversely simultaneously.

The actuating element 9 comprises an actuation sensor detecting an actuation of the actuating element 9 in a predetermined first actuation axis $B_1^-$–$B_1^+$ of the actuating element and in a predetermined second actuation axis $B_2^-$–$B_2^+$ of the actuating element. Furthermore, a signal processing device 12 is provided in the operating unit 3 to process an actuation signal from the control device 4 (for the actuating element 9) and/or a changeover signal from the changeover switch 11.

The signal processing device 12 can alternatively also be integrated into the control device 4 or it can be provided as a separate assembly in the operating unit 3 or in the surgical table 1.

The actuation sensor detects the actuation (or a signal corresponding to a requested actuation) in the first actuation axis $B_1^-$–$B_1^+$ and supplies a respective actuation signal to the signal processing device 12. The actuation signal depends on a direction $B_1^-$, $B_1^+$ of the actuation in the first actuation axis $B_1^-$–$B_1^+$. Similarly, the actuation sensor supplies a further actuation signal to the signal processing device 12 when an actuation in one of the directions $B_2^-$, $B_2^+$ in the second actuation axis $B_2^-$–$B_2^+$ is detected. Also here, the actuation signal depends on the direction $B_2^-$, $B_2^+$ of the actuation in the second actuation axis $B_2^-$–$B_2^+$. The actuation axes $B_2^-$–$B_2^+$ form an actuation coordinate system.

When an actuation of the actuating element 9 in the first actuation axis $B_1^-$–$B_1^+$ is detected so that the actuation signal is supplied to the signal processing device 12 and the changeover switch 11 does not supply a changeover signal to the signal processing device 12, the control device 4 activates the drive for the longitudinal displacement L. Activating the drive for longitudinal displacement causes the drive to displace the surgical tabletop 2 along the longitudinal direction. When the processing device receives or obtains a changeover signal from the changeover switch 11 in addition to receiving or obtaining an actuation signal from the actuation sensor for actuation of the actuating element 9 in the first actuation axis $B_1^-$–$B_1^+$, the control device activates the drive for the tilt T into a Trendelenburg or Anti-Trendelenburg position. Thus, by the actuation along the longitudinal direction of the surgical tabletop 2 and the actuation of the changeover switch 12, the control device 4 activates a rotation around a rotational axis perpendicular to the longitudinal displacement L (i.e., pitch rotation). Accordingly, the changeover signal is a rotation signal and the actuation signal specifies the axis of rotation and the direction.

The control device 4 drives the surgical table 2 for transverse displacement Q when an actuation of the actuating element 9 in the second actuation axis $B_2^-$–$B_2^+$ is detected so that the actuation signal is supplied to the signal processing device 12 and the changeover switch 11 does not supply a changeover signal to the signal processing device 12.

When the processing device 12 receives or obtains a changeover signal from the changeover switch 11 in addition to receiving or obtaining an actuation signal from the actuation sensor corresponding to actuation of the actuating element 9 in the second actuation axis $B_2^- - B_2+$, the control device drives the surgical table for the tilt K. Thus, by an actuation of the actuating element 9 in the transverse direction of the surgical tabletop 2 and the actuation of the changeover switch 12, the control device 4 activates a rotation around a rotational axis perpendicular to the transverse displacement Q (i.e., roll rotation).

In particular embodiments, the actuating element 9 may be configured for displacement along a single axis and/or rotation about a single axis perpendicular to the axis of displacement.

Furthermore, in alternative embodiments, the surgical tabletop is rotated due to the actuation signal and in case of a combination of the actuation signal and the changeover signal, the tabletop executes a longitudinal displacement.

The above described allocations are true if the actuation element 9 is attached to the surgical tabletop 2 such that the actuation coordinate system (e.g., the coordinate system of the actuation element 9) is aligned such that the first actuation axis $B_1^- - B_1+$ is parallel to the longitudinal axis of the surgical tabletop 2, therefore, also parallel to the longitudinal displacement L, and the second actuation axis $B_2^- - B_2+$ is parallel to the transverse axis of the surgical tabletop 2, therefore, parallel to the transverse displacement V. In case of an arrangement of the operating unit 3 at another side of the surgical tabletop 2, embodiments disclosed herein provide a change of an alignment of the actuation coordinate system.

In particular embodiments, the operating unit 3 further comprises an acceleration sensor 13 as a direction sensor. The acceleration sensor 13 detects an acceleration of the operating unit 3 for detecting a direction of movement of an initiated movement. The acceleration sensor 13 supplies a direction signal according to the direction of movement of the operating unit 3 to the signal processing device 12.

In various embodiments, the operating unit 3 may include a plurality of acceleration sensors 13 respectively detecting the acceleration in a plurality of directions. Particular embodiments include an optical sensor configured to detect a relative movement with respect to a stationary object, e.g. a floor or the column of the surgical table 5, and configured to supply a respective direction signal to the signal processing device 12.

The detection of the direction of movement of an initial movement of the operating unit 3 by means of the acceleration sensor 13 takes place immediately after a movement of the surgical tabletop 2 is driven by the actuating element 9. The signal processing unit 12 then compares the actuation signal and the direction signal.

When the direction signal and the actuation signal respectively correspond to a movement of the operating unit 3 and an actuating movement of the actuating element 9 being directed in the same direction, a control signal according to the actuation signal in the actuation coordinate system in the actual alignment relative to the operating unit 3 is supplied to the control device 4 and the movement is continued in the direction of the initial movement.

When the direction signal and the actuation signal respectively correspond to the movement of the operating unit 3 and the actuation movement of the actuating element 9 being directed in opposite directions, the actual alignment of the actuation coordinate system is rotated about 180 degrees around an axis here being perpendicular to the actuation axes $B_1^- - B_1+$ and $B_2^- - B_2+$. Thus, a control signal according to the actuation signal in the rotated actuation coordinate systems, therefore, opposite to the initial movement, is supplied to the control device 4.

When the direction signal and the actuation signal respectively correspond to the movement of the operating unit 3 and the actuating movement of the operating element 9 being directed in directions having a square angle with respect to another, the actual alignment of the actuation coordinate system is rotated about 90 degrees or 270 degrees around an axis being perpendicular to the actuation axes $B_1^- - B_1+$ and $B_2^- - B_2+$ and a control signal according to the actuation signal in the rotated actuation coordinate system, therefore, rotated about 90 degrees or 270 degrees with respect to the initial movement, is supplied to the control device 4. This case occurs when the operating unit 3 is attached to one of the front sides of the surgical tabletop 2.

In a case of a movable element of the medical apparatus having further possibilities for attachment of the operating unit 3 at different alignments to the directions of movement beyond those expressly and exemplarily recited herein, the actuation coordinate system is rotated according to the difference of the angles between the direction of actuation and the direction of movement of the initial movement also, as the case may be, around an axis not being perpendicular with respect to the axes of movement.

The signal processing device 12 is connected to the control device 4 and it supplies a control signal depending on the actuation signal, the changeover signal, and the direction signal to the control device 4 in order to drive the drives for the requested movement.

Figure 4:
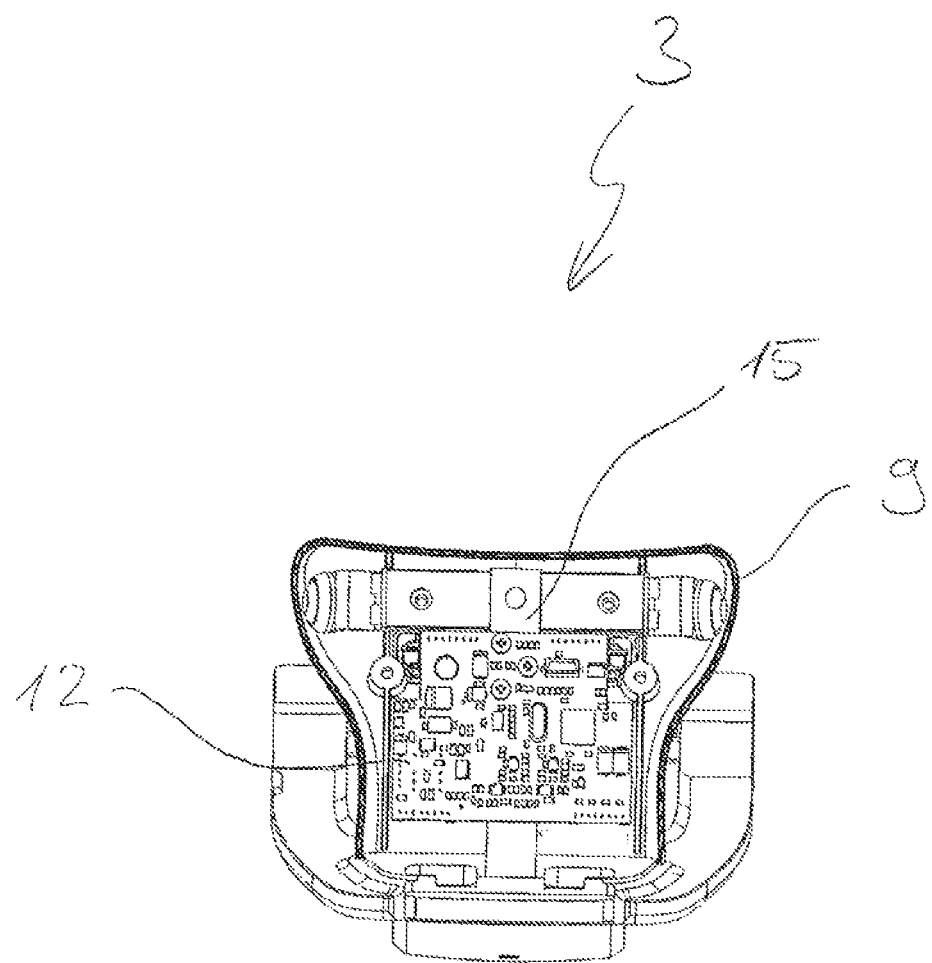
FIG. 4 is an illustration of the operating unit without a cover of an actuating element.

FIG. 4 shows the operating unit 3 without a cover on the actuating element 9. In FIG. 4, a force sensor is shown as the actuation sensor 15 for detecting the actuation of the actuating element 9. The force sensor supplies a signal depending on the direction in the actuation axis $B_1^- - B_1+$, $B_2^- - B_2+$ and also depending on the magnitude or rate of the actuating force to the signal processing unit 12. Accordingly, the control device 4 is configured to drive the drives such that the speed of a movement of the surgical tabletop 2 corresponds (directly or by a pre-determined factor) to the magnitude or rate of the actuating force.

In case of the detection of the actuating force in more than one actuation axis, therefore, e.g. in a longitudinal direction and a transverse direction, both respective signals are supplied to the signal processing device 12. The number of the detected actuation axes depends on the embodiment of the actuation sensor 15 and/or on the number of the actuation sensors 15 implemented. When a height adjustment of the surgical tabletop 2 is controllable by means of the actuating element 9, the actuation sensor 15 is configured to detect a respective actuating force in a longitudinal direction, a transverse direction, and a vertical direction. Alternatively, three actuation sensors 15 each of them respectively detecting an actuation force in one direction can also be provided.

FIGS. 5 and 6, respectively, show principle illustrations of a detection of a geometric characteristic of a first feature (FIG. 5) or a second feature (FIG. 6) of the surgical tabletop 2 by means of different embodiments of the operating unit 3 and of a fixing component on the side of the medical apparatus including, but not limited to, a standard rail or a surgical tabletop 2.

In FIG. 5, the first feature includes a chamfer 16 of the surgical tabletop 2. The operating unit 3 comprises a direction sensor (not shown) switched by an actuator 17.

In FIG. 5, on the left, the chamfer feature 16 does not exist, whereas in FIG. 5 on the right, the chamfer 16 is present so that different direction signals are supplied to the signal processing device. In FIG. 5 on the left, one side of the surgical tabletop 2 is depicted without the chamfer. The actuator 17 is actuated by a side face of the surgical tabletop 2 and the direction sensor gives the respective direction signal to the signal processing device. On the opposite side of the surgical tabletop 2 illustrated on the right, the chamfer 16 exists and, thus, the actuator 17 is not actuated by the side face. Therefore, contrary to the actuation, no or another direction signal is supplied to the signal processing device.

In FIG. 6, a groove 18 of the surgical tabletop 2 is shown as an alternative second feature. The operating unit 3 comprises the direction sensor (not shown) switched by the actuator 17.

In FIG. 6, on the left, the second feature does not exist, whereas, in FIG. 6 on the right, the second feature exists so that different direction signals are supplied to the signal processing device. In FIG. 6 on the left, a side of the surgical tabletop 2 is illustrated without groove. The actuator 17 is actuated by the side face of the surgical tabletop 2 and the direction sensor gives the respective direction signal to the signal processing device. On the opposite side of the surgical tabletop 2 illustrated on the right, the groove 18 exists and, thus, the actuator 17 is not actuated. Therefore, contrary to the actuation, no or another direction signal is supplied to the signal processing device.

The direction sensor provides the direction signal for the signal processing device 12 based on the detection or absence of the groove 18. The signal processing device 12 stores which side of the surgical tabletop is provided with the feature so that the processing device 12 can distinguish between the operation unit being attached to one side of the surgical tabletop 2 with respect to the other side.

FIG. 7 shows a principle illustration of an embodiment of the operating unit 3 alternatively detecting a magnetic field as a distinguishing feature between sides. In embodiments where the operating unit 3 distinguishes between sides of tabletop 2 based on a magnetic field, the operating unit 3 comprises a magnetic sensor 19, such as a reed switch or a Hall sensor. The magnetic sensor operates as the direction sensor. On one side (here illustrated on the left), the surgical table top 2 is provided with a magnetic strip 20 creating the magnetic field. The magnetic sensor 19 detects the presence of the magnetic field of the magnetic strip 20. Accordingly, the magnetic sensor provides one signal to the signal processing device 12 based on the magnetic strip for one side of the surgical tabletop 2, and the magnetic sensor provides another signal to the signal processing device 12 based on the absence of the magnetic strip for the other side of the surgical tabletop 2 to distinguish between the two sides of the surgical tabletop 2.

Another embodiment of the operating unit 3 is shown in FIG. 8. In FIG. 8, the operating unit 3 comprises a first plug-in device 21. The first plug-in device 21 is provided with a first contact device 22 on a first side of the surgical tabletop 2. The apparatus includes a second plug-in device 23 having a second contact device 24 on a second side of the surgical tabletop 2. In the embodiment illustrated in FIG. 8, a polarity of a voltage applied to the second contact device 24 is different than a polarity of a voltage applied to the first contact device 22. Thereby, a respective direction signal according to the polarity is given to the signal processing device 12 by the operating unit 3 based on attachment location of operating unit 3 to the tabletop 2. The signal processing device is configured to store which side of the surgical tabletop 2 has which polarity in order to subsequently distinguish the sides of the tabletop 2 when the operating unit is connected.

The contact devices 22, 24, are provided in a plug-in device 21, 23 by way of example only and are not limited solely thereto. In various embodiments, the contact devices 22, 24 may include touching contacts (surface contacts, etc.) or they may include touch-less contact connections including, but not limited to, as optical signal lines, strip lights, light barriers, capacitive contact systems, and inductive contact systems. The contact devices 22, 24 enable a fixing of the operating unit 3 along the side of the movable element at an arbitrary position, therefore, not in a defined given grid.

In another embodiment, the contact devices may be provided at positions displaced from the operating unit 3 via a communication unit that is configured for communicably connecting to the operating unit 3.

The number of the features 16, 18, 19 or the design of the contact devices 22, 24 is depicted here such that a differentiation of two sides is possible. By modifications of the features, as e.g. another quantity or another spatial arrangement, however, more than two sides can also be distinguished. Also, the geometric characteristics can be different and corresponding features can have different measurable attributes, for example grooves having different depths can be provided and used for distinguishing different sides. For example, the direction sensor may be configured to measure the depth of each groove and distinguish which side the operating unit 3 is attached to based on the measured or distinguished depths. Thus, by a coding system, there, various embodiments may supply different position signals for all sides of the surgical tabletop to the signal processing device 12.

Example embodiments can implement a combination of features for differentiation of sides.

In use, after an initialization of the operating unit 3, a so-called "freefloat" mode having an initially aligned actuation coordinate system is set.

The actuation coordinate system is either initially aligned by means of the features 16, 18, 19, by means of the design of the contact devices 22, 24, or it is aligned according to an at last stored alignment.

In case of an alignment according to the features or according to the contact device, or if, in an identification of the direction, the direction of actuation corresponds to the directions of movement, the control device 4 drives the drives in the "freefloat" mode. In the freefloat mode, the direction of actuation in the initially aligned actuation coordinate system is activated upon an actuation of the actuating element 9 in the first actuation axis $B_1^- - B_1^+$, the longitudinal displacement L is activated and upon a actuation of the actuating element 9 in the second actuation axis $B_2^- - B_2^+$, the transverse displacement Q is driven according to the direction of actuation. An actuation of the actuating element 9 having components in both axes $B_1^- - B_1^+$, $B_2^- - B_2^+$ leads to a superimposed control of the longitudinal displacement L and the transverse displacement Q.

Upon the actuation of the changeover switch 12 and the actuation of the actuating element 9 in the first actuation axis $B_1^- - B_1^+$ or the second actuation axis $B_2^- - B_2^+$, the tilt T into the Trendelenburg or Anti-Trendelenburg position or the tilt K of the surgical tabletop 2 is controlled in the "freefloat" mode.

In various embodiments, a release switch may be implemented. Actuation of the actuating element 9 for performing a movement of the surgical table may be predicated on simultaneously actuating the release switch and the actuating element 9 before permitting movement of the surgical table 1.

In case of the embodiment having the direction sensor detecting the direction of movement of the operating unit 3, the control of a movement leads to a control signal according to the initially aligned actuation coordinate system to the control device 4. Thereby, the direction of actuation of the actuating element 9 in the initially aligned actuation coordinate system is detected and a respective actuation signal is supplied to the signal processing device 12. The direction of movement of an initial movement of the surgical table top 2 and, therefore, of the operating unit 3 is detected by the direction sensor and the direction signal is also supplied to the signal processing device 12. In the signal processing device 12, the actuation signal and the direction signal are compared and if the direction signal corresponds to a direction of movement of the operating unit 3, the movement of the surgical tabletop 2 is continued in this direction. In the case, in which the direction of movement of the operating unit 3 does not correspond to the direction of actuation of the actuating element 9, the actuation coordinate system is rotated accordingly so that the direction of the movement of the operation unit 3 corresponds to the direction of actuation of the actuating element 9. The direction of movement of the surgical table top 2 is then changed according to the actuation signal in the rotated actuation coordinate system. This procedure takes place upon each actuation of the actuating element 9 so that a continuous movement of the surgical tabletop 2 takes place upon an unchanged positioning of the operating unit 3. In case of each change of the position of the operating unit 3, however, a correction of the allocation of the direction of actuation and direction of movement of the surgical tabletop 2 immediately takes place.

In case of the embodiments in which the specific features of the surgical table top 2 are detected or the design of the contact device is detected, the allocation of the features to the sides of the surgical tabletop 2 are stored in the signal processing device 12 and the initial alignment of the actuation coordinate system accordingly takes places.

The various embodiments disclosed herein may be combined to one another.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. An operating unit, for a medical apparatus having a driven movable element, comprising:
    a fixing device for coupling the operating unit to the driven movable element;
    an actuating element coupled to the fixing device;
    at least one actuation sensor adapted to detect an actuation of the actuating element in at least one predetermined actuation axis ($B_1^- - B_1+$, $B_2^- - B_2+$), wherein the at least one actuation sensor is adapted to supply an actuation signal based on the detected direction of actuation of the actuating element in the actuation axis ($B_1^- - B_1+$, $B_2^- - B_2+$);
    a signal processing device communicably coupled to the at least one actuation sensor; and
    at least one direction sensor communicably coupled to the signal processing device, wherein the at least one direction sensor is adapted to detect a direction of movement of the operating unit and to supply a respective direction signal;
    wherein the signal processing device is adapted to compare the direction signal and the actuation signal, to align an actuation coordinate system according to a result of comparison such that the direction of movement of the operating unit is equal to the direction of actuation, and to supply a control signal according to the actuation signal in the aligned actuation coordinate system to a control device of the medical apparatus.

2. The operating unit according to claim 1, wherein the at least one direction sensor is an acceleration sensor.

3. The operating unit according to claim 1, wherein the at least one direction sensor is an optical sensor adapted to detect a relative movement between the operating unit and a stationary object.

4. A method for operating a medical apparatus having an operating unit according to claim 1, comprising the following steps:
    detecting the directions of actuation ($B_1^-$, $B_1+$, $B_2^-$, $B_2+$) of the actuating element;
    supplying the control signal to the control device of the medical apparatus;
    detecting the direction of movement of the operating unit;
    comparing the direction of movement and the direction of actuation ($B_1^-$, $B_1+$, $B_2^-$, $B_2+$);
    if the direction of movement corresponds to the direction of actuation ($B1^-$, $B_1+$, $B_2^-$, $B_2+$), then, continuing the control signal;
    if the direction of movement corresponds to another direction than the direction of actuation ($B_1^-$, $B_1+$, $B_2^-$, $B_2+$), aligning the actuation coordinate system so that the direction of movement corresponds to the direction of actuation ($B_1^-$, $B_1+$, $B_2^-$, $B_2+$); and
    supplying the control signal in the aligned actuation coordinate system to the control device of the medical apparatus.

5. The method according to claim 4, further comprising:
    detecting a rotation signal via at least one changeover switch communicably coupled to the signal processing device, wherein the rotation signal drives a tilt corresponding to a rotation about a rotational axis perpendicular to the detected direction of the actuation signal; and
    supplying the control signal based at least in part on the rotation signal.

6. The operating unit according to claim 1, further comprising at least one changeover switch communicably coupled to the signal processing device, wherein the at least one changeover switch is adapted to provide a rotation signal, wherein the rotation signal drives a tilt corresponding to a rotation about a rotational axis perpendicular to the detected direction of the actuation signal, and
    wherein the signal processing device is further adapted to supply a control signal based at least in part on the rotation signal.

7. An operating unit for a medical apparatus having a driven movable element, wherein the movable element comprises a specific feature being different at attachment positions for the operating unit at different sides of the movable element and, wherein the operating unit comprises:
    a fixing device for coupling the operating unit to the movable element;
    an actuating element coupled to the fixing device;
    at least one actuation sensor adapted to detect an actuation of the actuating element in at least one predetermined actuation axis ($B_1^- - B_1+$, $B_2^- - B_2+$), the at least one actuation sensor adapted to supply an actuation signal based on the detected direction of actuation in the actuation axis ($B_1^- - B_1^+, B_2^- - B_2^+$);
a signal processing device communicably coupled to the at least one actuation sensor; and
at least one direction sensor communicably coupled to the signal processing device, the at least one direction sensor adapted to detect a direction of movement of the specific feature and to supply a respective direction signal to the signal processing device,
wherein the signal processing device is adapted to recognize the direction signal, to align an actuation coordinate system according to the direction signal such that the direction of movement of the specific feature is equal to the direction of actuation ($B_1^-, B_1^+, B_2^-, B_2^+$), and to supply a control signal according to the actuation signal in the aligned coordinate system to a control device of the medical apparatus.

8. The operating unit according to claim 7, wherein the at least one direction sensor is a magnetic sensor, and the specific feature is a magnetic field being different at different attachment positions of the movable element.

9. The operating unit according to claim 7, wherein the specific feature is a geometric characteristic of the movable element being different at the different attachment positions of the movable element.

10. The operating unit according to claim 9, wherein the geometric characteristic is a chamfer extending along at least one of the sides of the moveable element.

11. The operating unit according to claim 9, wherein the geometric characteristic is a groove extending along at least one of the sides of the moveable element.

12. The operating unit according to claim 7, further comprising at least one changeover switch communicably coupled to the signal processing device, wherein the at least one changeover switch is adapted to provide a rotation signal, wherein the rotation signal drives a tilt corresponding to a rotation about a rotational axis perpendicular to the detected direction of the actuation signal, and
wherein the signal processing device is further adapted to supply a control signal based at least in part on the rotation signal.

13. An operating unit for a medical apparatus having a driven movable element at least comprising a first side and a second side opposite to the first side, wherein the operating unit comprises:
a fixing device for coupling the operating unit to one of the sides of the movable element;
an actuating element coupled to the fixing device;
at least one actuation sensor adapted to detect an actuation of the actuating element in at least one predetermined actuation axis ($B_1^- - B_1^+, B_2^- - B_2^+$), the at least one actuation sensor adapted to supply an actuation signal based on a direction of actuation of the actuating element in the actuation axis ($B_1^- - B_1^+, B_2^- - B_2^+$);
a signal processing device communicably coupled to the at least one actuation sensor; and
a first contact device collaborating with a second contact device on the first and second sides of the moveable element, wherein a respective different direction signal is applied at the second contact device on the first side and the second side of the movable element,
wherein the signal processing device is adapted to recognize the direction signal, to align an actuation coordinate system according to the direction signal such that a direction of movement of the operating unit is equal to the direction of actuation ($B_1^-, B_1^+, B_2^-, B_2^+$), and to supply a control signal according to the actuation signal in the aligned actuation coordinate system to a control device of the medical apparatus.

14. The operating unit according to claim 13, wherein the first contact device and the second contact device are adapted such that the operating unit is fixable at an arbitrary position along the first and second sides of the movable element.

15. The operating unit according to claim 13, wherein the signal processing device is integrated in the medical apparatus.

16. The operating unit according to claim 13, wherein the medical apparatus is configured for displacement and rotation.

17. The operating unit according to claim 13, wherein the medical apparatus is a patient support table.

18. The operating unit according to claim 17, wherein the patient support table is a surgical table.

19. The operating unit according to claim 13, further comprising at least one changeover switch communicably coupled to the signal processing device, wherein the at least one changeover switch is adapted to provide a rotation signal, wherein the rotation signal drives a tilt corresponding to a rotation about a rotational axis perpendicular to the detected direction of the actuation signal, and
wherein the signal processing device is further adapted to supply a control signal based at least in part on the rotation signal.

* * * * *